(12) United States Patent
Lalena et al.

(10) Patent No.: US 8,824,634 B2
(45) Date of Patent: Sep. 2, 2014

(54) CONFIGURABLE AEC SENSOR FOR AN X-RAY SYSTEM

(75) Inventors: Michael C. Lalena, Webster, NY (US); David H. Foos, Webster, NY (US); Xiaohui Wang, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 171 days.

(21) Appl. No.: 13/083,780

(22) Filed: Apr. 11, 2011

(65) Prior Publication Data

US 2011/0249792 A1    Oct. 13, 2011

Related U.S. Application Data

(60) Provisional application No. 61/323,476, filed on Apr. 13, 2010, provisional application No. 61/449,932, filed on Mar. 7, 2011.

(51) Int. Cl.
*H05G 1/42* (2006.01)
*A61B 6/00* (2006.01)
*A61B 6/08* (2006.01)

(52) U.S. Cl.
CPC . *A61B 6/08* (2013.01); *A61B 6/547* (2013.01); *A61B 6/461* (2013.01); *A61B 6/542* (2013.01); *A61B 6/587* (2013.01); *A61B 6/4266* (2013.01); *A61B 6/4405* (2013.01); *A61B 6/4208* (2013.01)
USPC ........................................... 378/97; 378/108

(58) Field of Classification Search
USPC .................................... 378/97, 108
See application file for complete search history.

(56) References Cited

U.S. PATENT DOCUMENTS

| | | |
|---|---|---|
| 4,017,858 A | 4/1977 | Kuipers |
| 4,246,486 A | 1/1981 | Madsen |
| 4,752,948 A | 6/1988 | MacMahon |
| 4,836,671 A | 6/1989 | Bautista |
| 5,241,578 A | 8/1993 | MacMahon |
| 5,388,143 A | 2/1995 | MacMahon |
| 5,539,798 A | 7/1996 | Asahina et al. |
| 5,550,889 A | 8/1996 | Gard et al. |
| 5,617,462 A | 4/1997 | Spratt |
| 5,751,783 A | 5/1998 | Granfors et al. |
| 5,949,811 A | 9/1999 | Baba et al. |
| 6,047,042 A | 4/2000 | Khutoryansky et al. |
| 6,154,522 A | 11/2000 | Cumings |

(Continued)

FOREIGN PATENT DOCUMENTS

JP    2000-023955    1/2000

OTHER PUBLICATIONS

International Search Report & Written Opinion, International application No. PCT/US2011/032020, date Nov. 22, 2011, 8 pages.

(Continued)

*Primary Examiner* — Hoon Song

(57) ABSTRACT

A method for sensing a level of ionizing radiation directed from a radiation source through a subject and toward an imaging detector, the method executed at least in part by a logic processor, obtains positional coordinate data that is indicative of at least a portion of the subject to be exposed to radiation and that defines a radiation measurement area relative to the subject. The method assigns one or more sensing elements to sense radiation within the radiation measurement area. A measurement signal is acquired from each of one or more assigned sensing elements.

12 Claims, 16 Drawing Sheets

(56) References Cited

U.S. PATENT DOCUMENTS

| | | | |
|---|---|---|---|
| 6,192,105 B1 | 2/2001 | Hunter et al. | |
| 6,208,710 B1 * | 3/2001 | Nagai | 378/108 |
| 6,327,336 B1 | 12/2001 | Gingold et al. | |
| 6,404,851 B1 | 6/2002 | Possin et al. | |
| 6,422,750 B1 | 7/2002 | Kwasnick et al. | |
| 6,702,459 B2 | 3/2004 | Barnes et al. | |
| 6,760,405 B2 | 7/2004 | Ruetten et al. | |
| 6,895,268 B1 | 5/2005 | Rahn et al. | |
| 6,942,385 B2 * | 9/2005 | Fadler et al. | 378/205 |
| 6,944,266 B2 | 9/2005 | Yamazaki et al. | |
| 6,950,492 B2 | 9/2005 | Besson | |
| 7,010,091 B2 * | 3/2006 | Hayashida et al. | 378/98.8 |
| 7,120,229 B2 | 10/2006 | Takasawa | |
| 7,156,553 B2 | 1/2007 | Tanaka et al. | |
| 7,345,274 B2 | 3/2008 | Nilsson | |
| 7,368,724 B2 | 5/2008 | Morii et al. | |
| 7,490,986 B2 | 2/2009 | Takekoshi et al. | |
| 7,519,155 B2 | 4/2009 | Mollus et al. | |
| 7,581,884 B1 | 9/2009 | Barnes et al. | |
| 7,601,961 B2 | 10/2009 | Franklin et al. | |
| 7,613,276 B2 | 11/2009 | Sendai | |
| 7,632,016 B1 | 12/2009 | Huang et al. | |
| 7,744,279 B2 | 6/2010 | Heath et al. | |
| 7,780,350 B2 | 8/2010 | Tranchant et al. | |
| 7,794,144 B2 | 9/2010 | Windt | |
| 7,798,710 B1 | 9/2010 | Barnes et al. | |
| 2002/0150215 A1 | 10/2002 | Barnes et al. | |
| 2002/0188194 A1 * | 12/2002 | Cosman | 600/426 |
| 2003/0165216 A1 * | 9/2003 | Walker et al. | 378/108 |
| 2004/0101100 A1 | 5/2004 | Morii et al. | |
| 2004/0105526 A1 | 6/2004 | Zhang et al. | |
| 2005/0058244 A1 | 3/2005 | Tanaka et al. | |
| 2005/0169425 A1 * | 8/2005 | Takasawa | 378/97 |
| 2006/0109958 A1 | 5/2006 | Ertel et al. | |
| 2006/0269114 A1 | 11/2006 | Metz | |
| 2007/0030957 A1 | 2/2007 | Pommi | |
| 2007/0244388 A1 | 10/2007 | Sato et al. | |
| 2007/0255087 A1 | 11/2007 | Minai | |
| 2007/0297569 A1 | 12/2007 | Saunders | |
| 2008/0130837 A1 | 6/2008 | Heath et al. | |
| 2008/0198968 A1 | 8/2008 | Takekoshi et al. | |
| 2008/0204012 A1 | 8/2008 | Krueger et al. | |
| 2008/0240346 A1 | 10/2008 | Kashiwagi et al. | |
| 2009/0060145 A1 | 3/2009 | Tranchant et al. | |
| 2009/0086926 A1 | 4/2009 | Wang et al. | |
| 2009/0136000 A1 | 5/2009 | Nishii et al. | |
| 2009/0180590 A1 | 7/2009 | Borgmann et al. | |
| 2009/0257561 A1 | 10/2009 | Okuno et al. | |
| 2010/0002831 A1 | 1/2010 | Maack | |

OTHER PUBLICATIONS

International Search Report & Written Opinion, International application No. PCT/US2011/032035, dated Dec. 19, 2011, 9 pages.
One-page brochure for EasyPos dental x-ray positioning system from website, Mar. 2010. hyphendev.fr file PubEasypos08v3.pdf.
International Search Report, International application No. PCT/US2012/0262212, dated Aug. 30, 2012, 2 pages.
Supplementary Partial European Search Report completed Apr. 29, 2014 for European Patent Application No. 11 76 9406, 1 page.
Supplementary European Search Report completed Mar. 5, 2014 for European Patent Application No. 11 76 9395.2, 2 pages.

* cited by examiner

CONFIGURABLE AEC SENSOR FOR AN X-RAY SYSTEM

CROSS REFERENCE TO RELATED APPLICATION

This application claims priority to Provisional Application Ser. No. 61/323,476, filed 13 Apr. 2010, entitled "MOBILE UNIT HAVING TUBE ALIGNMENT SYSTEM," in the name of Lalena, incorporated herein by reference.

This application claims priority to Provisional Application Ser. No. 61/449,932, filed 7 Mar. 2011, entitled "GRAPHIC USER INTERFACE FOR MOBILE UNIT," by Stagnitto, incorporated herein by reference.

This application relates to patent application U.S. Ser. No. 13/083,776 entitled "DISPLAY OF AEC SENSOR LOCATION" in the name of Lalena, filed on even date.

This application relates to patent application U.S. Ser. No. 13/083,765 entitled "EXPOSURE CONTROL USING DIGITAL RADIOGRAPHY DETECTOR" in the name of Wang, filed on even date.

FIELD OF THE INVENTION

The invention relates generally to the field of radiographic imaging and more particularly relates to apparatus and methods for control of exposure energy in an X-ray system.

BACKGROUND OF THE INVENTION

Automatic Exposure Control (AEC) apparatus are widely used in conventional diagnostic X-ray equipment to control X-ray exposure levels received by a patient. Using an AEC device can help to limit the amount of radiation that is received by sensing the radiation level at a suitable location in the exposure path and providing an output signal that indicates when sufficient radiation has been received. This output signal is then used to disable power to the X-ray emission components, thereby stopping the generation of ionizing radiation.

The schematic block diagram of FIG. 1A shows an X-ray imaging system 10 that is used to provide a radiographic image of a patient or other subject 14. When the technician operates a control 24, an X-ray source 16 generates the ionizing radiation that is used for exposure and for forming an image onto a detector 12. An Automatic Exposure Control (AEC) apparatus 20 has one or more sensor elements 22 that respond to incident radiation by generating a signal that indicates the amount of radiation received. A generator control 18 interprets this signal and responds to terminate x-ray emission at an appropriate point.

AEC sensor elements 22 are typically located at suitable locations just behind the patient or other subject 14 in order to sense the amount of radiation received over particular areas of subject 14. Sensor elements 22 may be individual sensor elements, or may be integrated into a panel that is positioned behind the patient, as suggested in FIG. 1A. In other embodiments, sensor elements 22 of the AEC apparatus 20 are provided on the surface of detector 12 or in the bucky or other holder that is used for retaining detector 12.

The basic schematic diagram of FIG. 1A can be used with any type of X-ray detector technology, that is, with film, with computed radiography (CR) plates, or with a digital radiography (DR) flat panel detector.

The plan view of FIG. 1B shows a conventional arrangement of AEC apparatus 20 having three sensor elements 22. In conventional use, AEC sensor elements 22 are in fixed positions in front of the X-ray detector 12; in some systems, detector 12 or a plate holding AEC sensor elements 22 can be rotated within the plane in order to position the sensor element 22 devices appropriately with respect to the patient. Signals from individual sensor elements 22 are collected and combined for transmission to generator control circuitry.

The use of a standard pattern of AEC sensor elements 22 in fixed positions, as shown in FIG. 1B can present some problems. AEC sensor elements 22 work best when placed behind the area of bone or tissue that is of most diagnostic interest. This area can differ from one patient to the next. In addition, patient body size and proportions vary over a range, so that no one fixed pattern of AEC sensor elements 22 works optimally for all patient sizes and for all imaging situations. Some compromise is made for imaging under particular conditions when using the conventional AEC arrangement.

In some conventional x-ray systems, one or more AEC sensor elements 22 can be disabled for a particular image, allowing the operator to compensate somewhat for differences in the anatomy being imaged or for patient positioning. However, this solution can mean less accurate detection of the exposure level and risks over- or under-exposure for obtaining the image of the patient or other subject.

Thus, it can be seen that a more flexible arrangement of AEC sensors would have advantages for adapting to different patients and to different imaging applications.

SUMMARY OF THE INVENTION

An object of the present invention is to address the need for greater flexibility in the use of AEC sensors in diagnostic imaging applications. Advantageously, methods and apparatus of the present invention provide an arrangement of AEC sensor elements that allows their individual addressing, enablement, and grouping, thereby allowing configuration of AEC sensors to suit the conditions of each particular x-ray exam.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the present invention there is provided a method for sensing a level of ionizing radiation directed from a radiation source through a subject and toward an imaging detector, the method executed at least in part by a logic processor and comprising: obtaining positional coordinate data that is indicative of at least a portion of the subject to be exposed to radiation and that defines a radiation measurement area relative to the subject; assigning one or more sensing elements to sense radiation within the radiation measurement area; and acquiring a measurement signal from each of one or more assigned sensing elements.

According to another aspect of the invention, there is provided an apparatus for sensing a level of ionizing radiation directed through a subject and toward an imaging detector, the apparatus comprising: a panel having a set comprising a two-dimensional array of sensor elements disposed between the subject and the imaging detector, wherein each sensor element in the set is individually addressable for providing an indicator signal corresponding to the amount of ionizing radiation received; a control circuit that is in communication with the two-dimensional array of sensor elements and that is responsive to entered instructions: to define one or more composite radiation measurement regions along the panel, wherein each of the one or more composite radiation measurement regions is formed as a proper subset of the set of sensor elements and has two or more sensor elements and has a boundary with respect to the panel; to adjust the boundary of the one or more composite radiation measurement regions within the panel by changing the corresponding proper subset; and to collect the indicator signals from each of the sensor elements in the one or more composite radiation measurement regions and to form an output signal according to the collected indicator signals; and a transmission channel that is in communication with the control circuit and that is energizable to transmit the output signal.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1A:
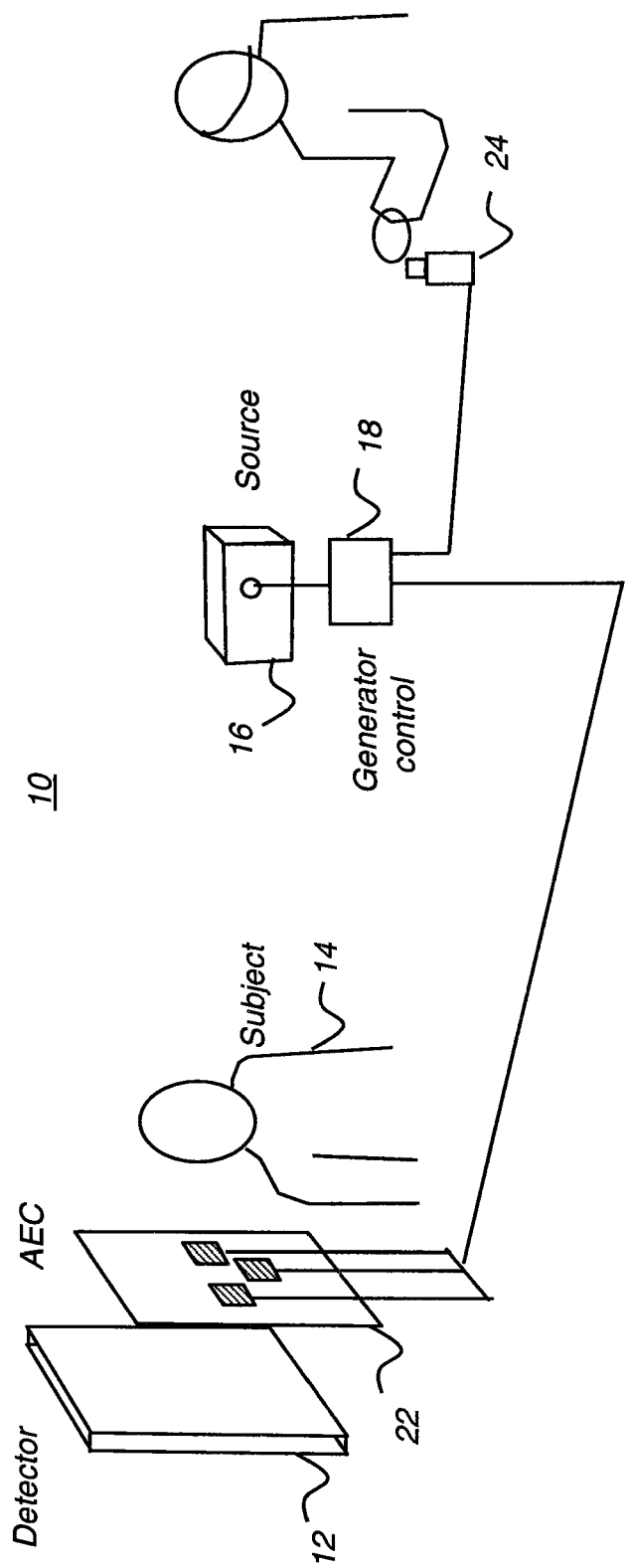
FIG. 1A is a block diagram showing components of a conventional radiographic imaging apparatus.

The following is a detailed description of the preferred embodiments of the invention, reference being made to the drawings in which the same reference numerals identify the same elements of structure in each of the several figures.

In the context of the present disclosure, the use of terms such as "first", "second", "third", etc., does not by itself connote any priority, precedence, or order of a component or claim element over another or the temporal order in which acts of a method are performed. These terms may be used more generally as labels to distinguish one element having a certain name from another element having the same name (but for use of the ordinal term) or to distinguish the claim elements.

The term "set", as used herein, refers to a non-empty set, as the concept of a collection of elements or members of a set is widely understood in elementary mathematics. The term "subset", unless otherwise explicitly stated, is used herein to refer to a non-empty proper subset, that is, to a subset of the larger set, having one or more members, but fewer members than the larger set. In formal set theory, one possible type of subset of a set S, that is, an "improper subset", may comprise the complete set S. A "proper subset" of set S, however, is strictly contained in set S and excludes at least one member of set S.

In the context of the present disclosure, the phrase "entered instructions" refers to control instructions that can be entered by an operator at an operator interface on a computer host (as described subsequently) or instructions stored in or generated by a program, such as in memory that is accessible to a computer or logic controller circuit. The term "actuable" relates to a function that can be selectively performed, such as when initiated by a control signal. Similarly, the term "energizable" relates to a function or action that occurs when a device is energized, such as by switching on power to the device.

At least portions of the method of the present invention execute on a computer or other type of control logic processor, which may include a dedicated microprocessor or similar device. A computer program product used in an embodiment of the present invention may include one or more storage media, for example; magnetic storage media such as magnetic disk or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

It should be noted that the term "memory", equivalent to "computer-accessible memory" in the context of the present disclosure, can refer to any type of temporary or more enduring data storage workspace used for storing and operating upon image data and accessible to a computer system. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

The apparatus and methods of the present invention help to resolve the problems experienced when using conventional, fixed-position AEC devices by providing an adaptable arrangement of individually addressable sensor devices in an AEC panel or other configuration. For example, this feature enables an AEC panel to be configured appropriately for the size and overall build of each particular patient and with consideration for the type of tissue that is being imaged in each case.

Figure 2A:
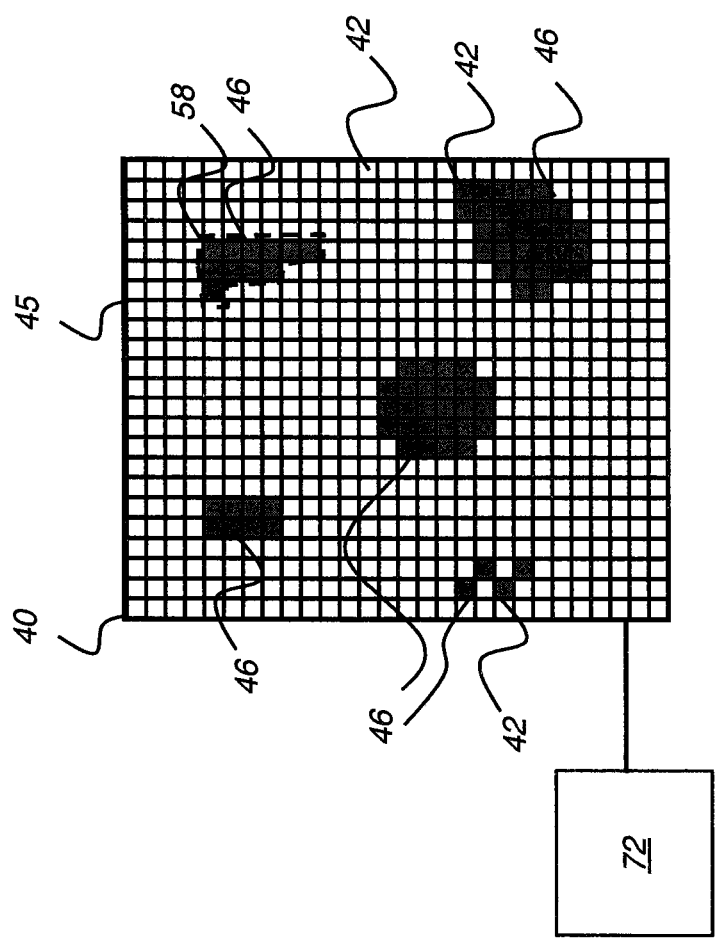
FIG. 2A is a plan view of an AEC apparatus with selectable sensor elements according to one embodiment of the present invention.

Referring to FIG. 2A, there is shown a configurable AEC apparatus 40 for sensing the level of ionizing radiation received according to one embodiment of the present invention. AEC apparatus 40 is configured as a two-dimensional array of sensor elements 42, arranged in rows and columns on a panel 45 in the embodiment shown. In the arrangement of FIG. 2A, each individual sensor element 42 is individually addressable to provide a measurement signal indicative of the amount of ionizing radiation that it receives. Cells that appear to be grayed in the example of FIG. 2A indicate sensor elements 42 that are enabled or addressed for obtaining the measurement signal; cells with white background indicate sensor elements 42 that are not enabled, that is, not addressed in this example. Each enabled (grayed) cell forms part of a composite radiation measurement region 46.

In the example of FIG. 2A, AEC apparatus 40 provides a large set comprising a plurality of sensor elements 42, here the product (m×n) elements, in an array wherein m is the number of rows and n the number of columns. Using the rectangular array grid pattern of FIG. 2A, for example, where sensor elements 42 are arranged in an array with 28 rows and 23 columns, the full set of sensor elements has 28×23=644 members. One or more smaller, proper subsets of this set are then selected to be addressed for providing measurement signals according to entered instructions. The selected composite radiation measurement region or proper subset in this example can have as few as two members, as many as 643 members.

The array arrangement of sensor elements 42 can vary significantly from the row/column arrangement of equal-sized components shown in FIG. 2A and other figures in this specification. Sensor elements 42 can utilize ion chamber sensing, as in conventional AEC devices, or may employ some other type of radiation sensing mechanism. Neighboring sensor elements 42 may be substantially contiguous, as shown in FIG. 2A and in other exemplary figures of the present application, or may be spaced apart from each other, at consistent or variable spacing intervals. It can be appreciated that a grid of sensor elements extending fully across the length and width of detector 12 may be impractical, providing some elements that would seldom, if ever, be used for some detector 12 configurations. Thus, a strategic placement of selectable sensor elements 42 in a two-dimensional array pattern can be used, depending on the type of imaging apparatus or type of detector that is employed. Sensor elements 42 can be of the same dimensions or may have different dimensions and shapes.

The measurement signals correspond to the amount of incident ionizing radiation received by the subset of sensor elements 42 that are addressed within an assigned radiation measurement area. Each selected proper subset is considered to be a composite radiation measurement region 46, and measurement signals are obtained from this proper subset. Each composite radiation measurement region 46 has a boundary 58, shown in dashed line form for only one of the composite radiation measurement regions 46 in FIG. 2A. An AEC controller circuit 72 responds to entered instructions to assign and define each composite radiation measurement region 46 and, when needed, to adjust its boundary by changing the proper subset of sensor elements 42, thereby either resizing or shifting the spatial position of composite radiation measurement region 46.

As is shown in FIG. 2A, the selected sensor elements 42 in each enabled composite radiation measurement region 46 may be substantially contiguous. Substantially contiguous sensor elements 42 are adjacent or "nearest neighbors", contiguous or touching along an edge of the sensing area, forming composite radiation measurement region 46 as a larger block or pattern. Alternately, neighboring sensor elements 42 in a composite radiation measurement region 46 can be substantially contiguous along a corner with respect to each other. Because sensor elements 42 are discrete components, there is typically some small amount of space needed between adjacent or contiguous sensor elements 42 in panel 45. Two sensor elements 42 of given height and width dimensions H and W can be considered to be substantially contiguous wherein the spacing between them is less than either value H or W, preferably less than half of either value H or W, and more preferably, when the spacing between does not exceed 0.1 times the smaller of H or W.

As FIG. 2A also shows, an AEC controller circuit 72 is coupled with the array of sensor elements in configurable AEC apparatus 40. AEC controller circuit 72 contains the logic for defining one or more composite radiation measurement regions 90, including spatial position and area or size, and for collecting measurement signals from the selected sensor elements 42. AEC controller circuit 72 may be packaged with the array of sensor elements or may be separately provided, as described in more detail subsequently. The collected measurement signals are then used to generate the output signal that is transmitted for control of x-ray generation from the x-ray source. The collected measurement signals may be combined in a number of ways, such as summing, averaging, or using some other combination method.

Figure 2B:
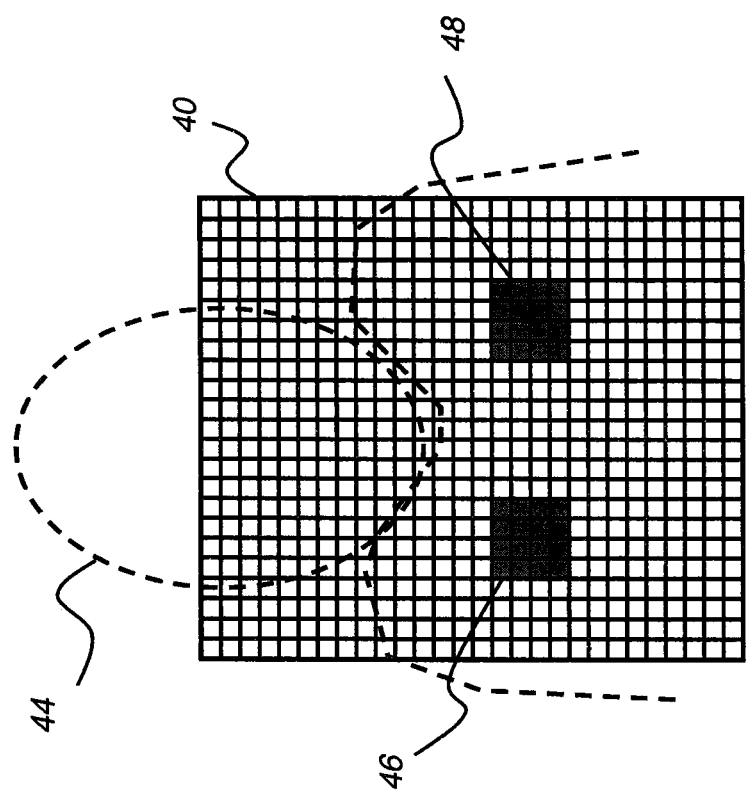
FIG. 2B is a plan view of an AEC apparatus with a selected pattern of composite radiation measurement regions.
Figure 2C:
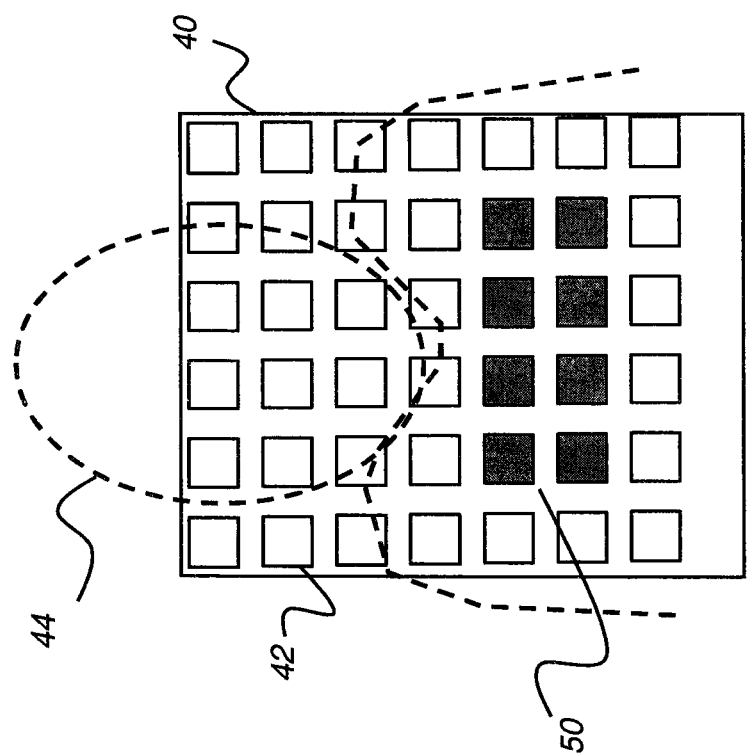
FIG. 2C is a plan view of an AEC apparatus with a single composite radiation measurement region selected.
Figure 2D:
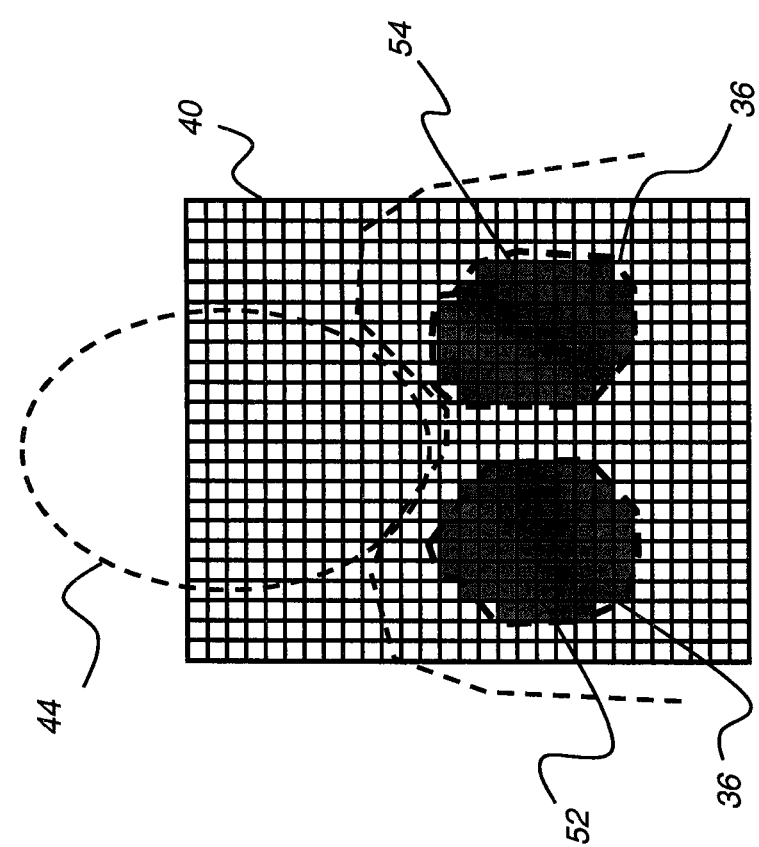
FIG. 2D is a plan view of an AEC apparatus with an alternate pattern of composite radiation measurement regions selected, configured to correspond to underlying tissue being imaged.
Figure 2E:
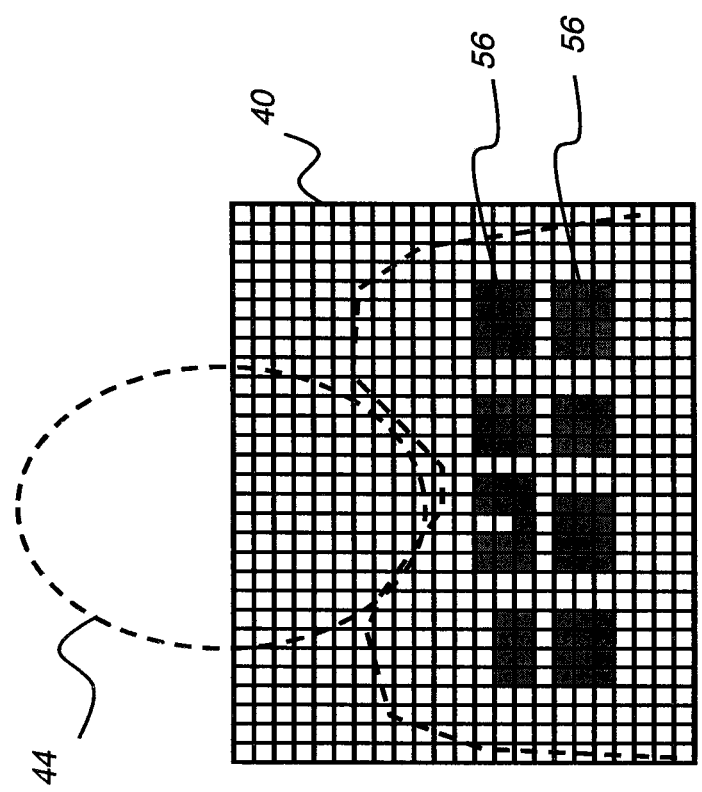
FIG. 2E is a plan view of an AEC apparatus with another alternate pattern of composite radiation measurement regions selected, with composite radiation measurement regions of different sizes.
Figure 2F:
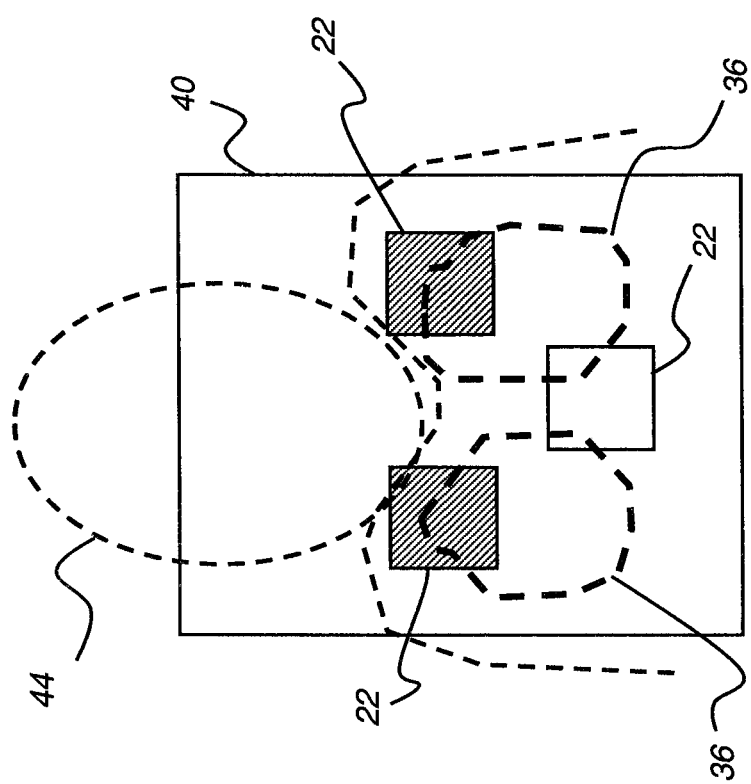
FIG. 2F is a plan view of an AEC apparatus with a conventional arrangement of non-composite radiation measurement regions, also usable in embodiments of the present invention.

FIGS. 2B-2F show various arrangements of the selected subset, as considered against an overlaid outline 44 of a patient or other subject, shown in dashed lines. In FIG. 2B, enabled sensor elements 42 are arranged in two composite radiation measurement regions 46 and 48. In FIG. 2C, enabled sensor elements 42 are grouped into a single composite radiation measurement region 50. Sensor elements 42 have a different size (area) and spacing in this embodiment from that shown elsewhere in the present application. FIG. 2D shows enabled sensor elements 42 arranged in composite radiation measurement regions 52 and 54 that approximate underlying organ tissue structures that are of interest. FIG. 2E shows an example of a distributed arrangement of composite radiation measurement regions 56 of different sizes and shapes. By way of comparison, FIG. 2F shows a conventional arrangement of fixed-position, fixed-size sensor elements 22, which can also be used in embodiments of the present invention, but often provide much less flexibility than other arrangements.

It is noted that, in an alternate embodiment of the present invention, AEC sensor elements 42 can be arranged in other than the generally rectangular row-column matrix arrangement shown in FIGS. 2A-2E. For example, sensor elements 42 can be provided as separate composite radiation measurement regions of regular or irregular shape. Moreover, sensor elements 42 may be in the form of discrete elements, mounted together and generally provided within the same plane of panel 45. In such an embodiment, sensor elements 42 may be movable, positionable along a platen or other holding device, held in place magnetically or using hook-and-loop fasteners or other type of coupling device.

Imaging Apparatus

Figure 3A:
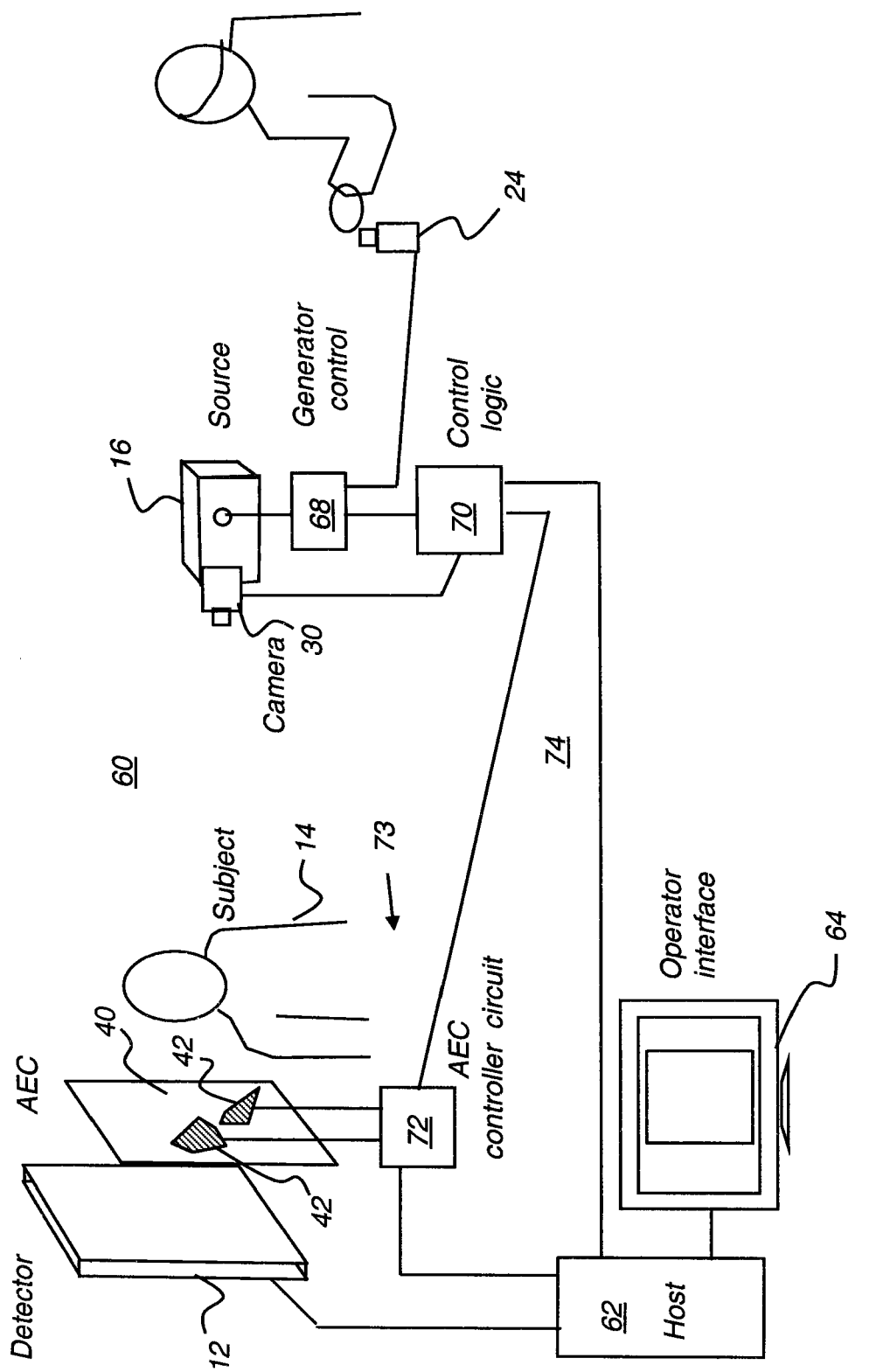
FIG. 3A is a block diagram showing components of a radiographic imaging apparatus using the AEC apparatus of the presentation with a wired transmission channel.
Figure 3B:
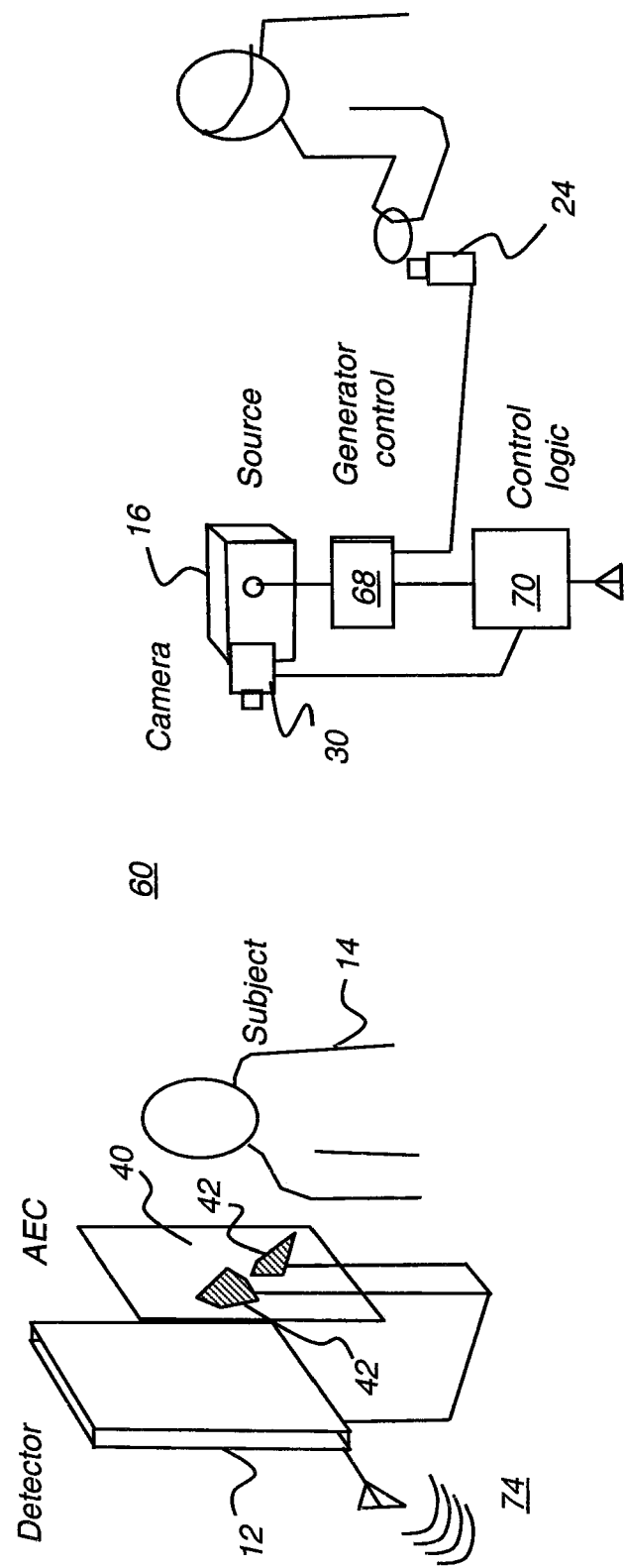
FIG. 3B is a block diagram showing components of a radiographic imaging apparatus using the AEC apparatus of the presentation with a wireless transmission channel.

By making the AEC device configurable to variations in patient build and to differences in types of tissue imaged, embodiments of the present invention enable the design of a more adaptive x-ray imaging apparatus that directs an appropriate amount of exposure for a particular image. The schematic block diagrams of FIGS. 3A and 3B show embodiments of an x-ray imaging apparatus 60 that provide this advantageous arrangement. It is noted that these block diagrams are in simplified form, are not drawn with intent to show actual scale, and show some components widely spaced apart with respect to the imaging axis in order to help simplify description. AEC components, for example, are typically spaced very close to the patient and to the detector in practice. Detector 12 can be any of a number of types of radiographic imaging detector, including a film cassette or other type of holder, a computed radiography (CR) detector, or a digital radiography (DR) detector. The embodiment shown uses a DR detector having an optional wire connection to a host computer 62. AEC apparatus 40 is typically positioned against or very near the surface of detector 12; FIGS. 3A and 3B extend this usual distance for better visibility of components relative to the following description.

FIGS. 3A and 3B show a number of functional control components that can be embodied in any of a number of alternative ways. For example, AEC controller circuit 72 can be a component that is integral to AEC apparatus 40 itself, or can be a separate component, or may be implemented as a function of detector 12, host computer 62, or some other component. Similarly, control logic circuit 70 can be combined with generator control 68 or may be implemented as a function of host computer 62 or some other suitable component. It can be appreciated by those skilled in the systems engineering and design arts that any number of arrangements for carrying out the functions of these control components are possible.

In the embodiment shown in FIG. 3A, as part of a sensing apparatus 73 that is actuable to configure the arrangement of sensor elements, host computer 62 connects to AEC controller circuit 72 that provides combined signals from the selected sensor elements 42 on AEC apparatus 40. An optional display 64 provides an operator interface for setup and selection or designation of enabled sensor elements 42, as described in more detail subsequently.

Still referring to FIG. 3A, a generator control 68 is energizable to initiate and terminate generation of the radiation signal from X-ray source 16. An optional control logic circuit 70 provides an interface between AEC controller circuit 72 and generator control 68. In one embodiment, control logic circuit 70 receives the combined signal from AEC controller circuit 72 and compares that against a threshold value to determine when to terminate the generation of radiation from X-ray source 16. In an alternate embodiment, wherein control logic circuit 70 is integral to host computer 62, host computer 62 performs the signal comparison and sends a terminating signal directly to generator control 68. A transmission channel 74 extends between the AEC controller circuit 72 and control logic circuit 70 for controlling the termination of x-ray generation by x-ray source 16. In the embodiment of FIG. 3A, transmission channel 74 is shown over a wire or cable, such as a fiber optic cable. In the embodiment of FIG. 3B, a wireless transmission channel 74 is used.

Turning now to FIG. 3B, in a wireless embodiment, the output signal from each of the enabled AEC sensor elements 42 is provided to on-board control logic in DR detector 12. This control circuitry is actuable to form a combined signal from these measurement signals and transmits the output signal to control logic circuit 70 for terminating the generation of X-rays.

From FIGS. 3A and 3B, it can readily be appreciated that a number of alternative arrangements are possible using either wired, including electrical or optical fiber connection, or wireless transmission of the combined signal that is generated from the individual AEC sensor element output signals. With the wired transmission channel 74 of FIG. 3A, the combined output signal can be an analog signal that is compared against a threshold value in generator control or control logic circuit 70. Alternately, a binary on/off signal can be provided based on comparing signal levels at the detector 12, at AEC apparatus 40, at AEC controller circuit 72, or at host computer 62. The wireless arrangement of FIG. 3B is better suited for generation of the combined signal as a digital value for transmission. It should also be noted that communication between AEC apparatus 40 and generator control 18 could be accomplished using wired or optical cable or wireless communication from the bucky or other component of the imaging system. Methods for combining the output signals from individual AEC sensor elements 42 can include averaging, weighting variability for particular AEC sensor elements 42, or threshold comparison directly with individual or summed output signals. As has been noted, various components shown, particularly AEC controller circuit 72, control logic circuit 70, host computer 62 and generator control 68 can be implemented in any of a number of ways. For example, a single hardware component can be used to perform all of the combined functions described.

Figure 4A:
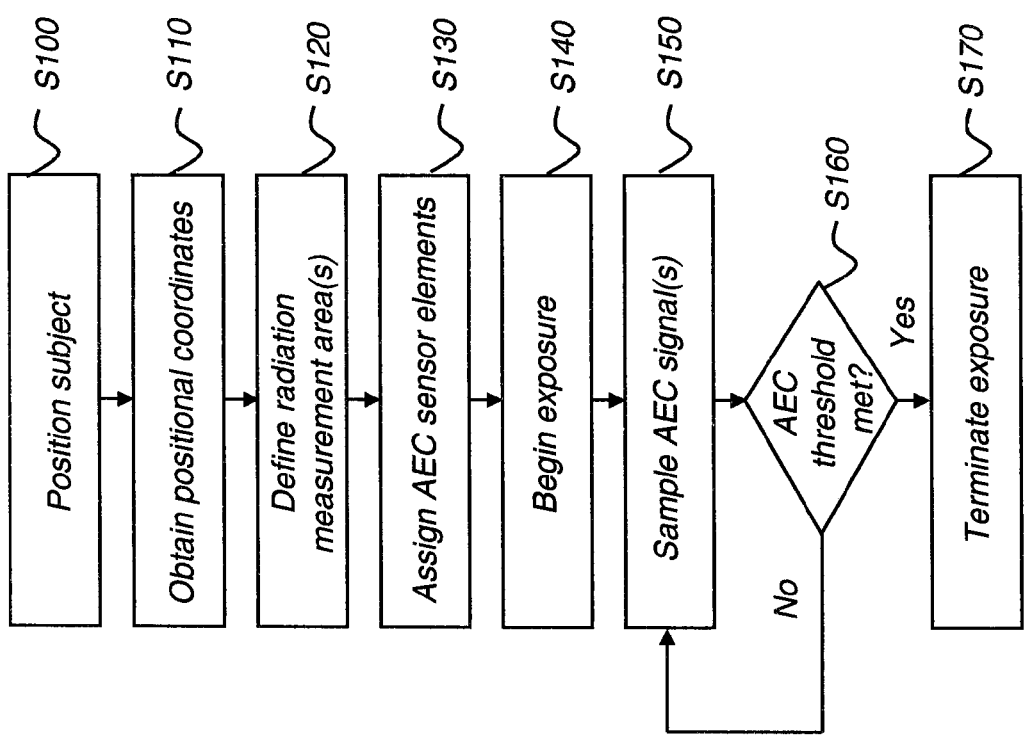
FIG. 4A is a logic flow diagram that shows a sequence of steps for determining when to terminate exposure using an embodiment of the present invention.

The logic flow diagram of FIG. 4A shows operational steps for terminating exposure using the AEC apparatus of the present invention. In a setup step S100, the subject is positioned in front of the detector and AEC apparatus. An obtain positional coordinates step S110 then obtains positional coordinate data that is indicative of the subject, or portion of a subject, that is to be exposed to radiation for obtaining an image. The positional coordinate data can be referenced to the subject and to the imaging detector. A define radiation measurement area step S120 then uses the positional coordinate data from step S110 to define a suitable radiation measurement area corresponding to the portion of the subject that is to be imaged.

Referring back to FIGS. 2D and 2F, for example, executing define radiation measurement area step S120 defines two desired radiation measurement areas 36, shown in bold dashed outline. In terms of relative spatial position, desired radiation measurement areas 36 correspond to those portions of the subject of most interest for radiation detection and measurement. A subsequent assign sensors step S130 then performs the actual mapping of desired radiation measurement areas 36 to sensor elements 22 or 42, depending on the sensor arrangement of the AEC apparatus in a particular embodiment.

Consistent with one embodiment of the present invention, the AEC device is highly adaptable for responding to measurement requirements. In the embodiment shown in FIG. 2D, for example, AEC apparatus 40 provides two composite radiation measurement regions 52 and 54 that correlate closely to desired radiation measurement areas 36 that were defined according to positional coordinate data. In one embodiment, outline 44 is displayed on an operator interface display, such as on display 64 (FIG. 3A). Outline 44 is obtained from a library of patient outlines, indexed by patient height, size, and other statistically obtained dimensional data.

Composite radiation measurement regions 52 and 54 are then automatically calculated in step S130, defined based on information about the positional coordinate data obtained using outline 44 and, optionally, according to information on the type of exam and other factors.

In an alternate embodiment of the present invention, as shown in FIG. 2F, the capability for setting up composite measurement regions is not available. In this case, the conventional arrangement of AEC apparatus 40 allows selection and use of only a small number of sensor elements 22, each of fixed area and fixed position. When desired radiation measurement areas 36 are defined, an attempt is made to provide a suitable arrangement of sensor elements based on what is available. In FIG. 2F, the upper two sensor elements 22, having substantial overlap corresponding to desired radiation measurement areas 36, are assigned in step S130. The lower sensor element 22, because it has only peripheral portions corresponding to the desired radiation measurement areas, is not assigned in this example. A number of alternate approaches can be used for steps S110, S120, and S130, each described in more detail subsequently.

Continuing to follow the sequence of FIG. 4A, assign sensors step S130 determines which of the AEC sensor elements are enabled for use as part of composite radiation measurement regions 46, to be addressed for obtaining their measurement signals as output. This sets up the variable AEC sensor configuration. A number of alternate embodiments can also be used for assign sensors step S130, as described in more detail subsequently.

Continuing with the FIG. 4A sequence, automatically executed steps follow a begin exposure step S140. Step S140 initiates exposure, activating the generator that provides x-ray radiation. As exposure commences, a sampling step S150 automatically executes, obtaining the measurement signals by periodically or continuously addressing the selected AEC sensor elements 42. A comparison step S160 checks the obtained measurement signal level against a reference threshold value in order to determine if exposure should be terminated. If the measured AEC measurement signals do not yet meet the threshold signal value, sampling step S150 is again executed and comparison step S160 repeated, until the threshold is met and a termination step S170 is performed to end exposure.

It can be appreciated that the sequence of steps shown in FIG. 4A is exemplary and admits a number of variations for measuring exposure energy and determining when to terminate x-ray generation. Define radiation measurement area step S120, for example, can be performed in a number of ways, based on the type of image that is obtained. Additional information about the type of exam, patient condition, pediatric information, or other factors may be used to execute assign sensors step S130. Operator-entered values may be used to change the overall behavior of AEC apparatus 40. Alternately, default operation without operator interaction can be used. The method described with reference to FIG. 4A can be used with an imaging system that obtains multiple images using a sequential sequence of exposures in pulsed form and acquires a measurement signal during this process; alternately, the process shown in FIG. 4A can be used with a system that applies radiation continuously until a termination signal is received.

Obtain Positional Coordinates Step S110

As was described with reference to the sequence of FIG. 4A, positional coordinate data is obtained for the subject, so that it can be used to define and configure the radiation measurement area that is used. The positional coordinate data itself can take any of a number of forms and relevant coordinate data can be stored in a computer-accessible memory, for example. Methods and approaches for obtaining and storing positional data that relate to components of an imaging system are known to those skilled in the imaging arts.

Figure 4B:
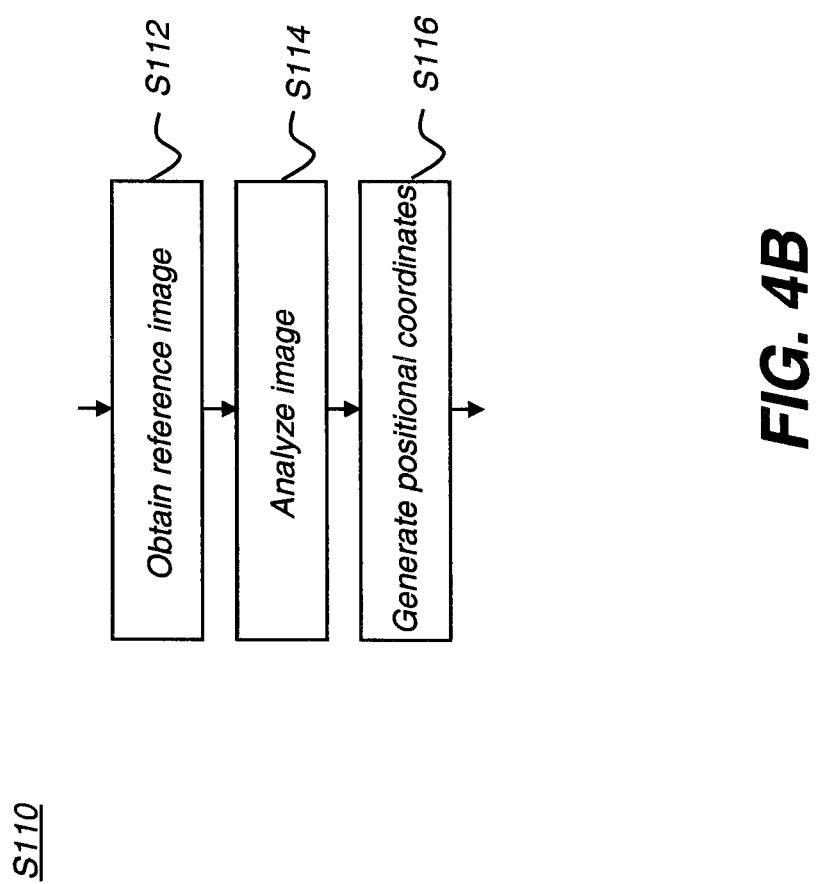
FIG. 4B is a logic flow diagram that shows a sequence of steps for obtaining positional coordinates according to an embodiment of the present invention.

FIG. 4B shows a sequence of steps for obtain positional coordinates step S110 according to an embodiment of the present invention. An optional reference image capture step S112 obtains an image of the subject that can be used as a reference to determine which AEC sensor elements to address for obtaining an output signal for the x-ray image. Using the configuration shown in FIG. 3A or 3B, for example, a camera 30 is actuable to obtain a reference image of the subject for use in determining which AEC sensor elements should be enabled. Camera 30 is aligned with x-ray source 16 in these embodiments. In an alternate embodiment using a DR imaging detector, an initial momentary radiation pulse is generated for generating reference image data from the detector, providing the positional coordinate data that will be used in configuring AEC sensor enablement. Advantageously, energy from this momentary radiation pulse can be added to subsequently provided radiation in order to obtain the exposure image from the detector. When the optional image is obtained in step S112, an analyze image step S114, executed on the host processor, for example, then analyzes the image data that is obtained in reference image capture step S112. A generate positional coordinates step S116 then generates the needed positional coordinates for indicating the portion of the subject that is to be exposed to radiation and for defining one or more radiation measurement areas. The image data can also be used to help in operator configuration of AEC sensors on display 64, as described in more detail subsequently.

When a radiation pulse is used as part of step S112, an outline of the patient can be readily obtained when using the grid arrangement shown in FIG. 2A. By evaluating the measurement signals, sensor elements 42 subjected to radiation that is not obstructed by the subject can be clearly distinguished from sensor elements 42 that lie behind the subject, relative to the x-ray source 16.

In an alternate embodiment, information about the patient, provided by the operator or from patient medical history or other source, is used to obtain positional coordinate information. For example, the relative build of the patient, the type of exam, and relevant data from earlier exams can be used to generate or to modify default positional coordinate data. A standard profile can be provided for outline 44 (FIGS. 2B-2F), displayed to an operator as a check on calculated results.

Automatic generation of positional data can be fairly straightforward where the position of the patient is somewhat fixed relative to the imaging detector and AEC or other sensing device. Assumptions on relative position can then be made with reasonable likelihood for anatomy to be imaged in such a case. With more portable x-ray systems, however, patient positioning relative to the detector can vary from one exam to the next, so that additional positioning information is often helpful. In one embodiment, manual entries by a technician are used to indicate patient position or to adjust default position or sizing for radiation sensing.

Assign Radiation Measurement Area Step S120

Referring back to FIG. 4A, step S120 for defining the radiation measurement area can be performed in a number of ways, based on the results of step S110. Automatic assignment can be performed, in which the host computer 62 or other processor designates an area within which one or more sensor elements 42 are desired. In an alternate embodiment, the assigned radiation measurement area is defined by the technician, such as by tracing out the area on an operator interface, as described in more detail subsequently.

In one embodiment of the present invention, step S120 that defines the radiation measurement area and step S130 that assigns AEC sensor elements are executed in a single operation. When using the conventional AEC apparatus of FIG. 1B, for example, there is no flexibility in determining the size (area) or position of sensor elements 22; these components are of fixed size and position. This simplifies the sequence of FIG. 4A, but is a limited solution in terms of flexibility and adaptability to specific exam requirements for a particular patient. In an alternate embodiment, when using an apparatus that allows configurable size and position of radiation sensing areas by grouping two or more sensing elements in a proper subset selected from the full set of available sensing elements, steps S120 and S130 can be considered separately. Step S120 defines the desired area for radiation measurement; step S130 then provides assignment of specific sensors corresponding to the desired area, in one embodiment allowing for operator adjustment in particular cases.

In an alternate embodiment, a technician can define the desired radiation measurement area by using a pointer or indicator when standing by the patient, as described in more detail subsequently.

Assign Sensors Step S130

Assign sensors step S130 can be executed in a number of ways. Consistent with one embodiment, the assignment is executed using entered instructions on display 64 or from instructions entered using touch sensors on the AEC apparatus 40 itself, as described in more detail subsequently. Consistent with an alternate embodiment, programmed assignment allows a default set of composite radiation measurement regions 46 to be automatically used unless changed by an operator. Pre-programmed instructions, obtained from a computer-accessible memory or storage medium, are executed in order to apply logic processing to the problem of AEC sensor element selection, such as on host computer 62 (FIG. 3A). Thus, for example, computer logic is used to configure an arrangement of AEC sensor elements such as those shown in the examples of FIGS. 2A-2F. The arrangement that is selected can be from a pre-stored pattern, one of a set of possible patterns for selection, or computed from information derived about the type of imaging exam that is to be performed and about the outline of the patient, computed from an obtained image or obtained from a stored outline approximating patient height and size, as described earlier with respect to step 110. It is noted that assignment or enablement of AEC sensor elements refers to whether or not the elements are addressed for providing their respective output signals during exposure. All sensor elements 42 may be provided with power for operation, but only those that are addressed provide their measurement signals as output for exposure measurement. In one embodiment, assigned AEC sensor elements are identified and their addresses listed in a memory buffer, which is then used to access measurement signal information from each listed element periodically or continuously during exposure.

Consistent with one embodiment, assign sensors step S130 also optionally includes setup procedures for configuring the response of one or more of the sensor elements 42. Adjustments can be made to adjust the sensitivity level or to set an exposure threshold in mAs or other unit, for example. This setup relates to the type of measurement signal provided from each sensor element 42 and to how the respective measurement signals may be combined and used in subsequent processing. In an alternate embodiment, no operator adjustment is needed and aspects of sensor element 42 grouping and response are automatically assigned and used unless changed.

Selection of Subset

Figure 5A:
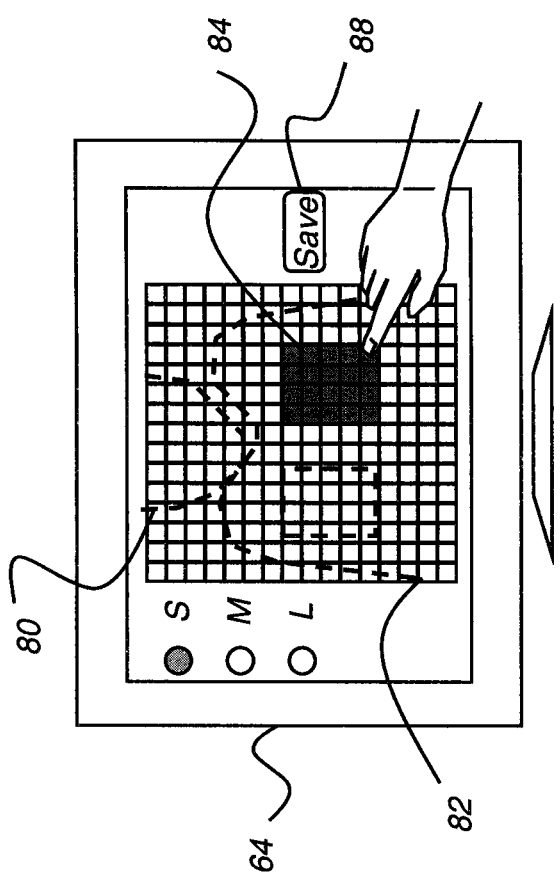
FIG. 5A is a plan view of a display showing technician configuration of an AEC apparatus.

Embodiments of the present invention allow the technician to select, by way of entered instruction, which sensor elements 42 of AEC apparatus 40 are used for a radiographic image. In the embodiment shown in FIG. 5A, display 64 is used as a type of control console for sensor element 42 selection. An optional outline image 80 of the patient or other subject is overlaid over an image 82 of AEC apparatus 40, aligned with corresponding sensor elements on the AEC apparatus. In the embodiment shown, patterns of predefined composite radiation measurement regions 84 are presented for operator selection, such as using a touchscreen selection as shown or using a mouse, joystick, or other suitable pointer. A Save command 88 enables the selected sensor elements 42 and allows the technician to proceed with the imaging process. With this arrangement, for example, the technician is presented with a small number of options, such as Patient size: Large, Medium, or Small in a menu selection or using a radio button 92 on the operator interface. Current view information, such as information on anatomy to be imaged, projection information, and patient position, can also be entered or obtained from setup data. Selection in this field then adjusts the composite radiation measurement region 84 arrangement automatically, without the need for visualization or use of positioning by the technician. Alternately, technician adjustment may be permitted.

In one embodiment, the selection of the subset of sensor elements for assign sensors step S130 employs information about the patient that is available from other networked sources, such as age and height or other data from a patient record, or from image type and setup information or from previous x-rays, stored in a DICOM system or other database. Auxiliary information about the type of the image obtained and the power levels used can also indicate patient size. Thus, for example, information about patient size can be derived indirectly or otherwise obtained and used for specifying the size (area) and position of composite radiation measurement region 46.

Figure 5B:
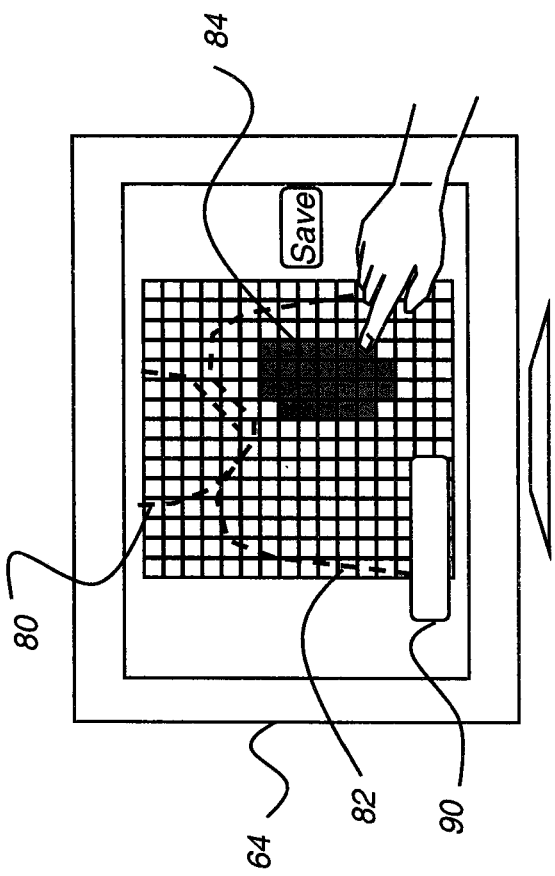
FIG. 5B is a plan view of a display showing technician configuration of an AEC apparatus using a traced pattern on a touchscreen.

FIG. 5B shows a more interactive arrangement that gives the technician additional flexibility for making sensor element 42 selections and thereby adjusting the boundary, position and size, of the composite radiation measurement region. Here, the position and boundary of composite radiation measurement region 84 is traced out by the technician, such as using a touchscreen as shown. The technician can outline an area to select all sensor elements 42 within the outline. Optionally, the technician can separately enable or not use any individual sensor element 42 in the array. The technician can also perform operations that spatially shift the position of one or more composite radiation measurement regions 84, such as moving composite radiation measurement region 84 upwards or downwards according to patient height or build. This can be done using "drag and drop" manipulation utilities, keyboard commands, or other instruction entry. Resizing of composite radiation measurement region 84 may also be executed by the technician. It can be appreciated that any of a number of user interface utilities could be used to adjust position or size of composite radiation measurement regions 46.

Also shown in FIG. 5B is an entry window 90 for the technician to specify the exposure level or signal level threshold for a particular composite radiation measurement region 84 or, in one embodiment, individually for each of the two or more sensor elements 42 within composite radiation measurement region 84. In one embodiment, window 90 displays when the technician configures or points to a particular composite radiation measurement region 84, allowing value entry or adjustment. Window 90 can alternately be used for entering data related to adjustment of AEC calibration values.

Figure 5C:
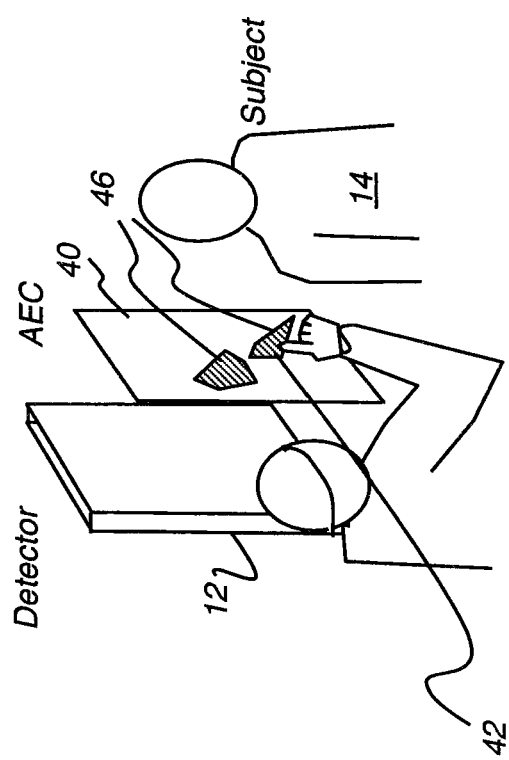
FIG. 5C is a perspective view showing technician selection of AEC sensor elements directly on the AEC apparatus itself.
Figure 5D:
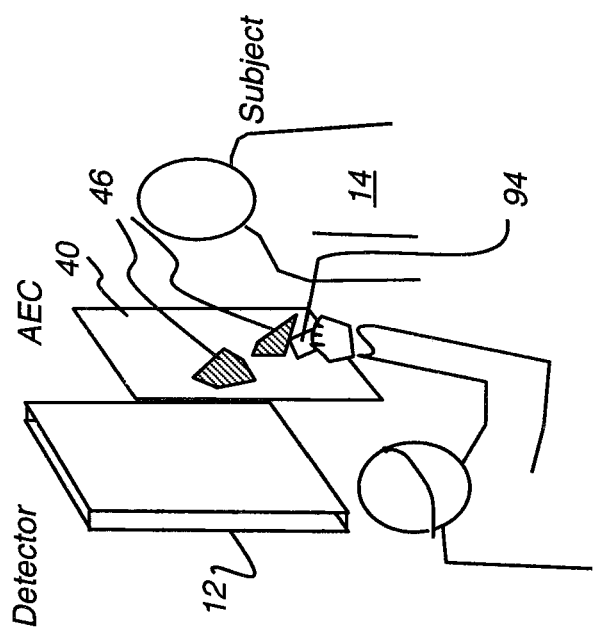
FIG. 5D is a perspective view showing technician selection of AEC sensor elements using an exposure switch.

The perspective view of FIG. 5C shows an alternate arrangement in which the technician selects the appropriate AEC sensor elements 42 on AEC apparatus 40 itself to form composite radiation measurement regions 46. Touch-sensitive elements (not shown) are provided to accept technician instructions on which underlying AEC sensor elements 42 are enabled. An audible beep or other indication is provided to verify selection of each sensor element 42. In one embodiment, a manual switch setting on AEC controller circuit 72 (FIG. 3A) is used by the technician to select which sensor element 42 is enabled. In an alternate embodiment, one or more of the AEC sensor elements 42 is movable, magnetically coupled to the surface of AEC apparatus 40.

Figure 1B:
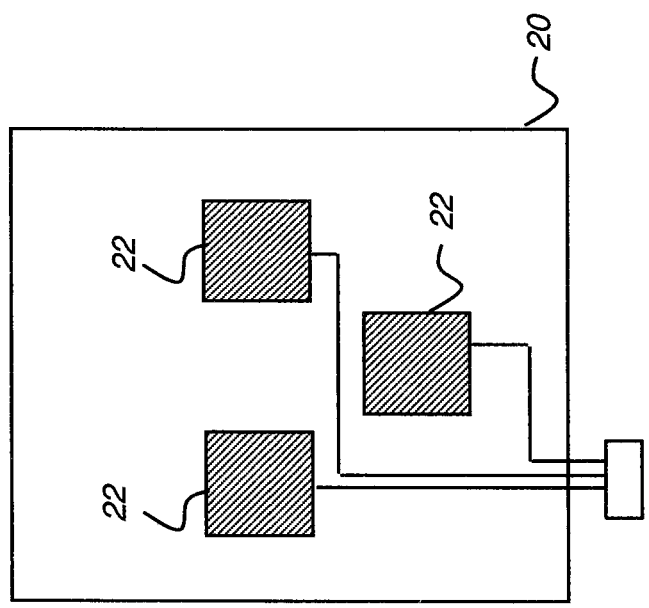
FIG. 1B is a plan view of an AEC apparatus having multiple sensor elements.

In yet another embodiment, an x-ray console could be utilized as the operator interface tool for AEC apparatus 40 setup. In one embodiment, as described earlier, a patient size setting is first performed by the operator, which simply adjusts the distance between sensor areas of apparatus 40 that will be used, thereby configuring AEC apparatus 40. The overall pattern of FIG. 1B is still used as a starting point; however, the technician or other operator can make corresponding changes to the subset grouping and position of AEC sensor elements to form suitable composite radiation measurement regions. This enables the technician to utilize an existing operator console interface in order to specify the desired signal level for x-ray termination.

Referring to the perspective view of 5D, there is shown an embodiment in which an exposure switch 94 or some other device is used as a type of hand-held pointer for defining the radiation measurement area (step S120 in FIG. 4A) and for positioning and sizing each composite radiation measurement region 46 on AEC apparatus 40 (step S130 in FIG. 4A). In one embodiment, placing and holding exposure switch 94 at a desired position adjusts the location and size of the corresponding composite radiation measurement region. Alternate pointing devices can be used. Related embodiments analyze and use technician gestures or audible commands for positioning and sizing composite radiation measurement regions 46. In one embodiment, the technician indicates, on the operator interface, which composite radiation measurement regions 46 to resize or to move. Then, a pointing device or technique of some type is used in order to reposition or resize the indicated composite radiation measurement region 46.

Consistent with an embodiment of the present invention, the position of each composite radiation measurement region 46 can be maintained regardless of the angle of orientation of detector 12 within the plane. Alternately, the composite radiation measurement regions 46 can be configured to rotate along with rotation of detector 12.

In general, where there are multiple composite radiation measurement regions 46, these regions are non-overlapping. However, there may be some overlap of boundaries between two composite radiation measurement regions 46 in various arrangements.

Consistent with one embodiment, information about the configuration of AEC apparatus 40 that is used for patient exposure is saved and stored as part of the DICOM metadata for the image.

It should be noted that, due to possible delays resulting from noise or other transmission problem, wireless communication can be less effective for transmitting commands and may not be error-proof in some environments. In one embodiment, a supplemental default timeout is applied to help reduce the likelihood of excessive exposure. This timeout value can be adjusted for variables such as patient size, imaging type, or other factors.

It is noted that while the present description and examples are primarily directed to radiographic medical imaging of a human patient or other subject, the apparatus and methods of the present invention can also be applied to other radiographic imaging applications. This includes applications such as non-destructive testing (NDT), for which radiographic images may be obtained and provided with different processing treatments in order to accentuate different features of the imaged subject.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. An apparatus for sensing a level of ionizing radiation directed through a subject and toward an imaging detector, the apparatus comprising:
   a panel having a set comprising a two-dimensional array of sensor elements disposed relative to the subject and the imaging detector, wherein each sensor element in the set is individually addressable for providing an indicator signal corresponding to the amount of ionizing radiation received;
   a control circuit that is in communication with the two-dimensional array of sensor elements and that is responsive to entered instructions:
      to define one or more composite radiation measurement regions along the panel, wherein each of the one or more composite radiation measurement regions is formed as a proper subset of the set of sensor elements and has two or more sensor elements and has a boundary with respect to the panel;
      to adjust the boundary of the one or more composite radiation measurement regions within the panel by changing the corresponding proper subset; and
      to collect the indicator signals from sensor elements in the one or more composite radiation measurement regions and to form an output signal according to the collected indicator signals; and
   a transmission channel that is in communication with the control circuit and that is energizable to transmit the output signal.

2. The apparatus of claim 1 wherein the two-dimensional array is a rectangular array.

3. The apparatus of claim 1 wherein the transmission channel transmits the output signal using wireless communication, wired communication, or optical fiber communication.

4. The apparatus of claim 1 wherein the transmission channel transmits the output signal to an X-ray generator or to a host computer.

5. The apparatus of claim 1 wherein the entered instructions are either (1) generated at a computer or (2) obtained from an operator action.

6. The apparatus of claim 1 wherein the control circuit is provided by a digital radiography imaging detector.

7. The apparatus of claim 1 wherein two or more of the sensor elements are substantially contiguous.

8. The apparatus of claim 1 wherein the transmission channel is further in communication with (1) an x-ray generator for controlling radiation or (2) a processor for controlling radiation.

9. A method for sensing a level of ionizing radiation directed through a subject and toward an imaging detector, the method comprising:

provide a panel for placement between a subject and an image-forming detector, the panel having a set comprising a two-dimensional array of sensor elements, wherein each sensor element in the set is individually addressable for providing an indicator signal corresponding to the amount of ionizing radiation that has been received;

accepting entered instructions to define one or more composite radiation measurement regions along the panel, wherein each of the one or more composite radiation measurement regions is formed as a proper subset of the set of sensor elements and has two or more sensor elements and has a boundary at a position within the panel;

redefining the boundary of the one or more composite radiation measurement regions within the panel to change the proper subset of the set of sensor elements according to one or more entered instructions;

collecting the indicator signals from each of the sensor elements in the one or more composite radiation measurement regions and forming an output signal according to the collected indicator signals; and transmitting the output signal.

10. The method of claim 9 wherein redefining the boundary comprises one of the following: (1) shifting the spatial position of any of the one or more composite radiation measurement regions within the panel, or (2) changing the area of any of the one or more composite radiation measurement regions within the panel.

11. The method of claim 9 wherein accepting the one or more entered instructions comprises one of the following: (1) obtaining an instruction from an operator, or (2) obtaining a stored instruction from a memory.

12. The method of claim 9 wherein forming the proper subset of sensor elements further comprises one of the following: (1) obtaining an image of the subject using visible light, or (2) obtaining an image of the subject using pulsed radiation energy.

* * * * *